(12) United States Patent
Sparks et al.

(10) Patent No.: US 11,160,612 B2
(45) Date of Patent: Nov. 2, 2021

(54) SYSTEM AND METHOD FOR COMPUTER-ASSISTED PLANNING OF A TRAJECTORY FOR A SURGICAL INSERTION INTO A SKULL

(71) Applicant: UCL Business LTD, London (GB)

(72) Inventors: Rachel Sparks, London (GB); Sebastien Ourselin, London (GB); John Duncan, London (GB)

(73) Assignee: UCL BUSINESS LTD, London (GB)

( * ) Notice: Subject to any disclaimer, the term of this patent is extended or adjusted under 35 U.S.C. 154(b) by 14 days.

(21) Appl. No.: 16/336,083

(22) PCT Filed: Sep. 22, 2017

(86) PCT No.: PCT/GB2017/052842
§ 371 (c)(1),
(2) Date: Mar. 22, 2019

(87) PCT Pub. No.: WO2018/055395
PCT Pub. Date: Mar. 29, 2018

(65) Prior Publication Data
US 2019/0209245 A1 Jul. 11, 2019

(30) Foreign Application Priority Data
Sep. 26, 2016 (GB) .................................. 1616283

(51) Int. Cl.
*A61B 34/10* (2016.01)
*G06T 19/00* (2011.01)
(Continued)

(52) U.S. Cl.
CPC ............ *A61B 34/10* (2016.02); *G06T 19/003* (2013.01); *A61B 2034/107* (2016.02);
(Continued)

(58) Field of Classification Search
CPC . A61B 34/10; A61B 2034/107; G06T 19/003; G06T 7/0012; G06T 2210/41; G16H 20/40
See application file for complete search history.

(56) References Cited

U.S. PATENT DOCUMENTS 6,112,750 A * 9/2000 Chandra ............. G06F 19/3481
128/898
2008/0123922 A1* 5/2008 Gielen ................. A61B 6/5241
382/131
(Continued)

FOREIGN PATENT DOCUMENTS

WO 2012092511 A2 7/2012
WO 2015173571 A1 11/2015
WO 2018055395 A1 3/2018

OTHER PUBLICATIONS

A method for planning safe trajectories in image-guided keyhole neurosurgery (Year: 2010).*
(Continued)

*Primary Examiner* — Nizar N Sivji
(74) *Attorney, Agent, or Firm* — Hamilton, Brook, Smith & Reynolds, P.C.

(57) ABSTRACT

A computer system and corresponding method are used to assist in planning a trajectory for a surgical insertion into a skull to a target representing an anatomical region. The computer system is configured to: provide the computer system with a three-dimensional image representation of the skull and brain which has been parcellated into anatomical regions, including an identification of critical objects comprising structures within the brain to be avoided during the surgical insertion; provide the computer system with a region of interest comprising an anatomical region within the brain representing the target of the trajectory for the surgical insertion; determine a metric for voxel locations
(Continued)

within the anatomical region corresponding to the region of interest, the metric representing the suitability of each of the voxel locations to be a target location for the trajectory; select a set of one or more voxel locations having the greatest suitability according to the metric within the region of interest, each of the one or more selected voxel locations representing a potential target location for the trajectory; and identify a trajectory for the surgical insertion to a potential target location in the region of interest.

19 Claims, 9 Drawing Sheets

(51) Int. Cl.
  *G16H 20/40* (2018.01)
  *G06T 7/00* (2017.01)
(52) U.S. Cl.
  CPC ........ *G06T 7/0012* (2013.01); *G06T 2210/41* (2013.01); *G16H 20/40* (2018.01)

(56) References Cited

U.S. PATENT DOCUMENTS

| | | | | |
|---|---|---|---|---|
| 2009/0259230 | A1* | 10/2009 | Khadem | A61B 34/20 606/130 |
| 2013/0211424 | A1* | 8/2013 | Thiran | A61B 90/14 606/130 |
| 2014/0003696 | A1* | 1/2014 | Taghva | A61B 34/10 382/131 |
| 2015/0297309 | A1* | 10/2015 | Bly | B29C 64/386 700/98 |
| 2016/0070436 | A1 | 3/2016 | Thomas et al. | |
| 2017/0076450 | A1* | 3/2017 | Sela | G06K 9/4661 |
| 2017/0309069 | A1* | 10/2017 | Thomas | A61B 5/055 |
| 2019/0090826 | A1* | 3/2019 | Carmi | A61B 6/037 |

OTHER PUBLICATIONS

Assessment of variability in cerebral vasculature for neuro-anatomical surgery planning in rodent brain (Year: 2011).*
Medical Image Computing and Computer-Assisted Intervention—MICCAI 2011 (Year: 2011).*
Image-based in vivo assessment of targeting accuracy of stereotactic brain surgery in experimental rodent models (Year: 2016).*
Baegert, et al., "Trajectory optimization for the planning of a percutaneous radiofrequency ablation of hepatic tumors," Computer Aided Surgery, 12(2): 82-90 (Mar. 2007).
Beare, R., et al., Finding regional extrema—methods and performance (2005), http://hdl.handle.net/1926/153.
Beriault, S., et al., "A multi-modal approach to computer-assisted deep brain stimulation trajectory planning," IJCARS, 7(5), pp. 687-704 (2012).
Cardoso, M., et al., "Geodesic Information Flows: Spatially-Variant Graphs and Their Application to Segmentation and Fusion," IEEE Transactions on Medical Imaging, vol. 34, No. 9 (Sep. 2015).
Essert, S., et al., "Automatic computation of electrode trajectories for Deep Brain Stimulation: a hybrid symbolic and numerical approach," IJCARS, 7(4), pp. 517-532 (2012).
Guo, et al., "Automatic Target and Trajectory Identification for Deep Brain Stimulation (DBS) Procedures," MICCAI 2007, Part I, LNCS 4791, pp. 483-490 (2007).
Shamir, R., et al., "Reduced risk trajectory planning in image-guided keyhole neurosurgery," Medical Physics, 39(5), pp. 2885-2895 (2012).
Zelmann, R., et al., "Improving recorded volume in mesial temporal lobe by optimizing stereotactic intracranial electrode implantation planning," IJCARS, 10(10), pp. 1599-1615 (2015).
Zombori, G., et al., "A Computer Assisted Planning System for the Placement of sEEG Electrodes in the Treatment of Epilepsy," IPCAI, pp. 118-127 (2014).
Zuluaga, M., et al., "Stability, structure and scale: improvements in multi-modal vessel extraction for SEEG trajectory planning," IJCARS, 10(8), pp. 1227-1237 (2015).
Duncan, J.S., "Imaging in the surgical treatment of epilepsy," Nat. Rev. Neurol., 6(10), pp. 537-550 (2010).
Klein, A., et al., "101 labeled brain images and a consistent human cortical labeling protocol," Frontiers in Neuroscience, 6(171) (2012).
Hartigan, J., et al., "Algorithm AS 136: A K-Means Clustering Algorithm," JSTOR, 28(1), pp. 100-108 (1979).
International Preliminary Report on Patentability for International Application No. PCT/GB2017/052842 entitled "A System and Method for Computer-Assisted Planning of a Trajectory for a Surgical Insertion Into a Skull," dated Mar. 26, 2019.
Sparks, et al., "Efficient Anatomy Driven Automated Multiple Trajectory Planning for Intracerebral Electrode Implantation," No Institute Given (2016).
Sparks, et al., "Efficient Anatomy Driven Automated Multiple Trajectory Planning for Intracerebral Electrode Implantation," Centre for Medical Image Computing et al. (2016).
De Momi, E., et al., Multi-trajectories automatic planner for StereoElectroEncephaloGraphy (SEEG), International Journal on Computer Assisted Radiology and Sugery, vol. 9, No. 6, Nov. 1, 2014.
Sparks, R., et al., "Efficient Anatomy Driven Automated Multiple Trajectory Planning for Intracranial Electrode Implantation," Network and Parallel Computing, Oct. 2, 2016.
International Search Report and Written Opinion for International Application No. PCT/GB2017/052842 entitled "A System and Method for Computer-Assisted Planning of a Trajectory for a Surgical Insertion Into a Skull," dated Dec. 14, 2017.

* cited by examiner

SYSTEM AND METHOD FOR COMPUTER-ASSISTED PLANNING OF A TRAJECTORY FOR A SURGICAL INSERTION INTO A SKULL

FIELD OF THE INVENTION

The present invention relates to a system and method for computer-assisted planning of a trajectory for a surgical insertion into a skull (intra-cranial insertion).

BACKGROUND OF THE INVENTION

Approximately one-third of individuals with focal epilepsy continue to have seizures despite optimal medical management, e.g. with anti-epileptic drugs. These patients are candidates for resection if the epileptogenic zone (EZ) can be identified (and then resected without impacting cortical function). In about 25% of surgical candidates, the EZ cannot be inferred from non-invasive imaging data [10]. These patients may undergo surgical intra-cerebral electrode implantation to record electoencephalography signals to help identify where seizures start and rapidly propagate. Implanted electrodes may also be used for stimulation studies to map eloquent areas, e.g. motor or sensory cortex, and to determine whether a safe resection may be made that removes the EZ without compromising eloquent cortex. However, such invasive procedures carry a risk of haemorrhage, neurologic deficit, and infection.

Electrodes are placed to assess (1) deep anatomical regions of interest (ROIs) (e.g. a hippocampus or insula), identified as a potential EZ, and (2) superficial ROIs, which are nearby functional areas around the potential EZ (e.g. motor or sensory cortex). The superficial ROIs are targeted to determine any overlap between the EZ and functional areas to aid in planning safe resection margins. The electrodes must avoid critical structures (e.g. blood vessels, sulci) to minimise the risk of complications such as haemorrhage.

Preoperative planning of electrode placement is a necessary prerequisite to implantation. Important anatomical and functional landmarks of the brain (such as blood vessels, pial boundaries, nerve tracts, etc.) can be identified with advanced neuro-imaging and image-processing techniques. Usually multiple electrodes are to be implanted, each electrode having a trajectory defined by a brain target and a skull entry. For example, a trajectory may extend from a respective entry point on the skull to a respective target point in a deep ROI. In particular, the trajectory for each electrode is selected to record from a deep ROI, and potentially one or more superficial ROIs, while also avoiding critical structures and interference with other electrodes. The overall configuration of electrodes to be implanted is arranged to achieve adequate cortical coverage and pass through safe, avascular planes.

The clinical gold standard for the preoperative planning of electrode placement is manual planning of each electrode trajectory by visual inspection of pre-operative imaging data. The trajectories are placed to attain dep and superficial ROIs, avoid critical structures, sample grey matter (GM), and avoid conflict between electrodes. Maximal sampling of GM is preferred, as epileptic seizures arise in GM rather than in white matter. However, such planning is a complex, time-consuming task. Automated trajectory planning algorithms can help to reduce planning time while improving safety and EEG signal acquisition (e.g. increased GM sampling) by optimising trajectories using quantitative measures of electrode path suitability.

Various single trajectory planning methods have been presented which require the user to specify a target as a point (spatial coordinate) [2, 6, 8] or a manually identified ROI. A potential trajectory is discarded if it is surgically infeasible, e.g. it the angle of entry at the entry point is too far from the normal, or the overall length of the trajectory is too long. A potential trajectory is further discarded if it passes an unsafe distance from any critical structures, such as blood vessels and sulci. The remaining trajectories (which have not been discarded) are scored and sorted according to a risk metric, and the most suitable trajectory is selected. However, these methods have certain limitations when applied to electrode implantation for epilepsy. For example, for epilepsy, clinicians have a list of target ROIs from which it is desired to obtain EEG signals, and the most suitable target point within each ROI may not be readily apparent. Furthermore, since multiple electrodes typically are to be implanted simultaneously, they must be placed to avoid conflicts between electrodes (while at the same time trying to maximise the coverage area for recording, e.g. the GM sampling).

Multiple trajectory planning algorithms designed for electrode implantation for epilepsy allow a user to identify target and entry regions [4, 7]. Reference [4] determines trajectories by randomly sampling from regions near user selected targets and entry points. For every target, the best trajectory in terms of entry angle, avoidance of critical structures, and lack of conflict between electrodes is computed. Reference [7] determines candidate target points within the hippocampus and amygdala by randomly sampling a Gaussian distribution defined on the ROI distance map, in which targets far from the surface of the ROI are preferentially sampled. Trajectories are removed from consideration if they intersect critical angles or have a surgically infeasible entry angle. Finally the best trajectories are determined by maximising grey matter capture, minimising risk score, and ensuring there is no mutual interference between trajectories. (Note that each electrode may have multiple contacts distributed along its length, each capable of recording a signal for that location, so that maximising grey matter sampling is therefore impacted by the placement of these individual contacts according to a given trajectory).

WO 2015/173571 (which is hereby incorporated by reference into the present application) describes a system and method for the computer-assisted planning of trajectories for surgical insertion into a skull, including determining a trajectory to a given target location, for example based on surgical feasibility, lack of interference with other electrode trajectories, and a low risk factor. As disclosed in WO 2015/173571, a user may specify that an electrode is to be placed within a particular anatomical region. It is suggested that this could be accomplished by computer sampling the specified region to provide a set of target locations, determining a trajectory to each of these target locations, and then selecting the target location within the region for which the respective trajectory has the lowest assessed risk. Although this approach provides an appropriate trajectory to a target point in the region, it is rather expensive in terms of computational resources, especially if electrodes are to be placed in multiple regions.

SUMMARY OF THE INVENTION

The invention is defined in the appended claims.

A method and apparatus are provided to assist in planning a trajectory for a surgical insertion into a skull to a target representing an anatomical region. The apparatus is configured to perform the method comprising: providing the computer system with a three-dimensional image representation of the patient anatomy comprising the skull and brain which has been parcellated into anatomical regions, including an identification of critical objects comprising structures within the brain (i.e. internal to the skull) to be avoided during the surgical insertion; providing the computer system with a region of interest comprising an anatomical region within the brain representing the target of the trajectory for the surgical insertion; determining a metric for voxel locations within the anatomical region corresponding to the region of interest, the metric representing the suitability of each of the voxel locations to be a target location for the trajectory; selecting a set of one or more (e.g. several) voxel locations having the greatest suitability according to the metric within the region of interest, each of the one or more selected voxel locations representing a potential target location for the trajectory; and identifying a trajectory for the surgical insertion to a potential target location in the region of interest.

The methods described here can be used to support planning a surgical insertion or incision for a wide range of clinical purposes. For example, the surgical incision may be utilised to implant an electrode for performing (stereo) electroencephalography. In this context, there may be multiple electrodes to insert, each involving planning a respective surgical incision. Other clinical purposes for planning a surgical insertion may be to insert a stent, to perform deep brain stimulation or a tumour biopsy, the placement of other probes in the brain: e.g. to drain cysts or ventricles, to introduce a medical laser device into a particular part by a safe trajectory, and/or to deliver focal therapy. (It will be appreciated that this listing of potential clinical purposes is by way of example only, and is not intended to be exhaustive).

It will be appreciated that the precise nature of the instrument or device being inserted will vary according to the particular clinical context, likewise the criteria utilised for assessing the suitability of any given trajectory. For example, for investigations relating to epilepsy, the criteria may include a cost function based on the proportion of the trajectory associated with an entry point which passes through grey matter compared with the proportion of the trajectory which passes through white matter. This is because the electrode may have the multiple contacts typically spaced along such an electrode, and these should be located in grey matter in order to obtain a desired signal. Having a higher proportion of the trajectory in grey matter increases the likelihood that the contacts will be located, as desired, in grey matter. However, this distinction between grey matter and white matter may be less (or not at all) relevant in other clinical contexts, such as for performing a tumour biopsy. Similarly, other aspects of the planning procedure may vary as appropriate according to the clinical context. For example, while major blood vessels are always expected to represent critical objects or structures to be avoided, the inclusion of certain other anatomical features as critical objects may depend upon the particular clinical context.

In some implementations, the computer system provides a graphical visualization of a trajectory which helps a user to understand better any risks associated with the trajectory, in particular, the portion(s) of the trajectory that is/are closest to critical structures. In some implementations, the graphical visualisation of a trajectory is linked to at least one two-dimensional or three-dimensional view derived by the computer system from the three-dimensional representation of the skull and of critical objects located within the skull.

Also provided is a computer program comprising program instructions in machine-readable format that when executed by one or more processors in a computer system cause the computer system to implement any of the various methods as described above. These program instructions may be stored on a non-transitory computer readable storage medium, such as a hard disk drive, read only memory (ROM) such as flash memory, an optical storage disk, and so on. The program instructions may be loaded into random access memory (RAM) for execution by the one or more processors of a computer system from the computer readable storage medium. This loading may involve first downloading or transferring the program instructions over a computer network, such as a local area network (LAN) or the Internet.

Also provided herein is an apparatus comprising a computer system configured to implement the various methods as described above. The computer system may comprise one or more machines, which may be general purpose machines containing one or more processors for running program instructions (as described above), configured to perform such methods. The general purpose machines may be supplemented with graphics processing cards units (GPUs) to provide additional processing capability, e.g. for parallel computations, such as assessing different target locations or different potential trajectories. The computer system may also comprise at least some special purpose hardware for performing some or all of the processing described above, such as determining the visualisations. The computer system may be incorporated into apparatus specifically customised for performing computer-assisted planning of a trajectory for a surgical incision. Such apparatus may also be used to provide support during the surgical operation itself, such as by providing real-time visualisations of the position of an inserted instrument (potentially in relation to the planned trajectory), and/or by providing visualisations of data acquired during the surgical operation.

BRIEF DESCRIPTION OF THE DRAWINGS

Various embodiments of the invention will now be described in detail by way of example only with reference to the following drawings.

DETAILED DESCRIPTION

Figure 1:
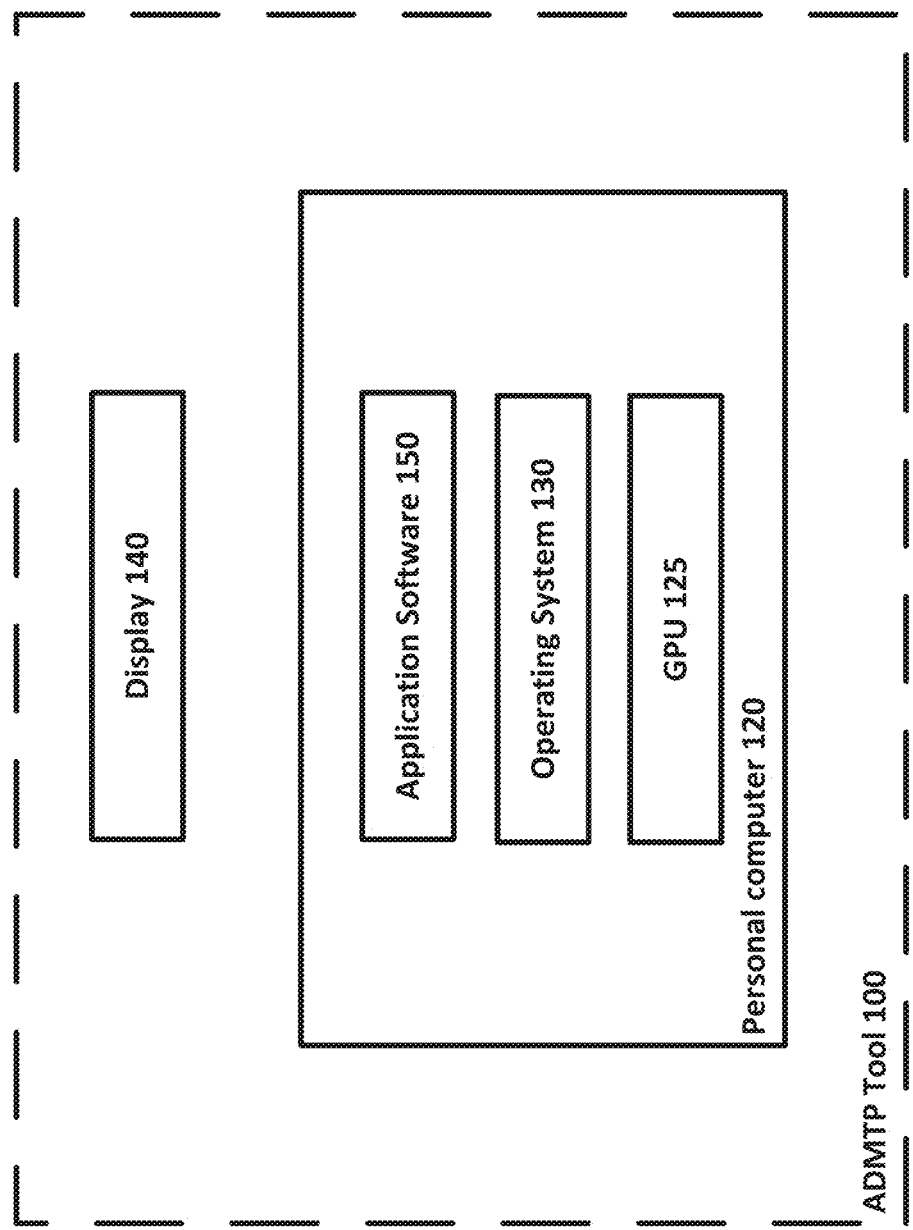
FIG. 1 is a schematic diagram of an interactive tool for computer assisted planning of intra-cranial surgical insertions in accordance with some embodiments of the invention.

Some embodiments of the present invention provide a tool for anatomy driven, multiple trajectory planning (ADMTP), which uses patient specific anatomy to compute trajectories. The ADMTP tool requires as user input only the anatomy names for the deep and superficial ROIs of interest (as described in more detail below). The ADMTP tool then selects target points within the specified deep ROIs according to safety, measured in terms of distance from critical structures. The best trajectories to these selected target points can then be computed to attain superficial ROIs, avoid critical structures, improve grey matter sampling, and avoid conflicts between electrodes.

A) METHODOLOGY

The ADMTP tool takes as input a patient specific image of the brain, which represents a 3-dimensional spatial map of the brain, corresponding to or derived from one or more images of the brain of the patient which have been acquired using any appropriate neuro-imaging technique(s). The patient specific image is annotated to provide parcellation and critical structure segmentation, in effect specifying anatomical regions within the brain and critical structures. For example, for parcellation, each pixel/voxel within the patient specific image is labelled according to the specific anatomical region that contains (or is represented by) that pixel. Critical structures (e.g. arteries, veins and sulci) are specifically identified and segmented, likewise grey matter is also identified. Note that a critical structure, such as a blood vessel, may pass through various anatomical regions (potentially including one or more region of interests).

In some implementations, this parcellation and/or segmentation may be performed at least part in automated fashion by computer. In addition, the parcellation and/or segmentation may be performed at least in part with respect to the original acquired images, and then transferred to the final patient specific image(s) of the brain to be used for trajectory planning. For example, blood vessels (veins and arteries) may be identified and segmented using computed tomography (CT) angiography and/or T1-weighted magnetic resonance imaging (MRI) with gadolinium enhancement using multi-scale, multi-modal tensor voting vessel extraction [9]. The skull can be segmented from CT data with thresholding and morphologic dilation. Geodesic information flow (GIF) [3] may be used to parcellate the brain from T1 weighted MRI data, for example, using the Desikan-Killiany-Tourville (DKT) protocol [11]. It will be appreciated that other implementations may use different approaches for performing the parcellation and/or segmentation, including if so desired manual parcellation and/or segmentation (by hand).

A user is now able to select various anatomical regions (as determined by the parcellation) as deep or superficial ROIs from the patient-specific image of the brain. In one example implementation, a total of 208 brain regions are identified by the parcellation, and are then available for selection as deep or superficial ROIs.

The ADMTP tool is provided with the parcellated imaging data, the segmented critical structures (objects), and a list of ROIs (deep and superficial). For a list of user-defined ROIs, ADMTP then finds an implantation plan $V(N)=[v_1, \ldots, v_N]$, where $v_n$ represents the trajectory for the $n^{th}$ electrode. For $v_n$, M candidate target points $T_{n,i}:i\in\{1, \ldots, M\}$ are calculated. ADMTP then determines P entry points $E_{n,j}$ $j\in\{1, \ldots, P\}$ for each $T_{n,i}$ and finds a combination of $T_{n,i}$ and $E_{n,j}$ for all N electrodes that avoids interference between the electrodes.

For a given ROI, target point selection determines M candidate target points $T_{n,i}:i\in\{1, \ldots, M\}$ for the $n^{th}$ electrode. A target risk image is defined as $C_t=[C, f_t(c):c\in C]$ where C is the grid of image voxel locations and $f_t(c)$ is the target risk score for the given voxel c. $f_t(c)$ is computed as:

$$f_t(c) = \begin{cases} 1, & \text{if } c \notin \Omega_{roi} \\ 1, & \text{if } c \in \Omega_{roi} \\ \omega_{roi}*\left(1-\dfrac{f_{roi}(c)}{\max(f_{roi})}\right) + \\ \omega_{cri}*\left(1-\dfrac{f_{cri}(c)}{\max(f_{cri})}\right), & \text{else} \end{cases} \quad \text{(Equation 1)}$$

In which $\Omega_{roi}$ is the set of voxels in the deep ROI, $\Omega_{cri}$ is the set of voxels in the critical structures, $f_{roi}$ is the distance between voxel c and the closest surface point on the deep ROI, calculated using a bounding volume hierarchy (BVH) as in [8]. Similarly, $f_{cri}$ is the distance between voxel c and the closest surface point on all critical structures. In addition, $\omega_{roi}$ and $\omega_{cri}$ control the relative importance of placing the target within the deep ROI and avoiding critical structures, respectively. Target points are selected from $c\in C_t$ by calculating local minima using the watershed algorithm [1] and then sampling the M lowest values of $f_t(c)$ with a distance of at least $d_{tar}$ between every target point $T_{n,i}$.

In other words, $f_t(c)$ has a value of 1 for any voxel that is not within the specified ROI, or that is within a critical structure. Such voxels will therefore not be selected as a target location for the specified ROI. The remaining voxels (which are inside the specified ROI but outside any critical structure) are candidate target locations. The selection between these candidate target locations is determined according to a metric based on two factors. The first factor represents the distance from (within) the surface of the ROI, normalised by the maximum distance of any candidate target location from the surface of the ROI, the second factor represents the distance from (outside) the nearest surface of a critical structure, normalised by the maximum distance to the nearest surface of a critical structure.

In general terms, it is good to be a long way from the nearest surface of a critical structure (because this enhances safety), i.e. increasing $f_{roi}(c)$; likewise, it is generally good to be a long way from the surface of the relevant ROI (e.g. because this can provide more reliable signal recording), i.e. increasing $f_{cri}(c)$. Each term in brackets in Equation 1 therefore ranges from unity (the voxel is located on the surface of the ROI or a critical structure), down to zero (the voxel is located at the maximum distance from the surface of the ROI or a critical structure), where a lower value is better. The metric is then based on the weighted sum of these first and second brackets (corresponding to the first and second factors), according to relative the values of $\omega_{roi}$ and $\omega_{cri}$ (such that a higher value of the weight gives the corresponding factor a relatively larger influence on the final value of the metric). In the case that $\omega_{roi}$ and $\omega_{cri}$ are chosen to sum to unity, then the metric ranges in value between zero and unity, with a lower score being better. For example, Table 1 (below) gives example values of 0.25 and 0.75 respectively for that $\omega_{roi}$ and $\omega_{cri}$, indicating that avoiding a critical structure (object) is given a higher weighting than depth inside the ROI.

Note that in Equation 1 above, $f_t(c)$ is defined so that a high value of the metric is good—i.e. more suitable. However, in other implementations, $f_t(c)$ might be defined so that a low value of the metric is more suitable. References herein to a maximum of the metric should be understood as indicating a (potentially local) high value of suitability.

It will also be appreciated that other approaches can be used for calculating the target risk score. For example, rather than determining $f_{roi}(c)$ based on the distance from the given location (c) to any surface of the ROI (as above), another way to determine $f_{roi}(c)$ is based on the proximity of the given location (c) to the medial surface of the ROI—i.e. the surface that faces the midline (plane of left-right symmetry). Having a location (c) close to the medial surface may be beneficial (more suitable) if it is desired to locate the electrode in deep grey matter.

Note that the calculation of the metric for voxel c is determined only from the location of c (and the surfaces of the ROI and any nearby critical structures). In particular, the value of the metric is not dependent upon any putative trajectory to voxel c. This allows the metric to be calculated relatively quickly (since there is no need to perform calculations along the length of a trajectory). Once the metric has been determined, a number of local maxima within the ROI are identified. For example, M target locations can be identified by sampling the M lowest values of $f_t(c)$, subject to a constraint that there is a distance of at least $d_{tar}$ between each target point $T_{n,i}$. These M target locations can be considered as promising end-points for a trajectory, because they are relatively deep inside the specified ROI, and relatively far away from any critical structure.

In another implementation for finding M target locations, iterative flooding [1] is used to find a set of voxels Q corresponding to local minima of $f_t(c)$. The voxels p, where p∈Q, are then spatially clustered into K groups using K-means clustering [12], where K is set equal to the number of electrodes to be located in that particular ROI. For the $k^{th}$ electrode, the final target points are the M points in the $k^{th}$ cluster with the highest values of $f_t(c)$.

Given the set of M target locations within the ROI as identified above, a trajectory to each target location within the ROI can be determined as follows. Entry points, defined as $E_{n,j}$: j∈{1, ..., P}, are computed by using all vertices on the skull mesh; in one implementation, this is roughly 10000 points sampled every 0.2 mm³. Potential trajectories $\overline{T_{n,i}E_{n,j}}$:i∈{1, ..., M}, j∈{1, ..., P}, are then removed from consideration using a modified approach of [8] as follows:
1. $\overline{T_{n,i}E_{n,j}}$ is longer than $d_{len}$.
2. The angle between $\overline{T_{n,i}E_{n,j}}$ and the skull normal is greater than $d_{ang}$.
3. $\overline{T_{n,i}E_{n,j}}$ does not traverse a desired superficial ROI.
4. $\overline{T_{n,i}E_{n,j}}$ intersects a critical structure (arteries, veins, or sulci).

If a trajectory falls into any of the above categories, it is excluded. If no suitable trajectories are found, the values of $d_{len}$ and/or $d_{ang}$ may be iteratively relaxed, for example $d_{len}$ may be stepped up by 10 nm (e.g. to a maximum of 110 mm), and/or $d_{ang}$ may be stepped up by 10° (e.g. to a maximum of 45°), until a suitable set of trajectories is found. For example, after the above filtering based on these hard criteria, typically there may be 1000-5000 potential trajectories per electrode. The remaining trajectories then have a risk score $R_{n,i,j}$ and a GM ratio $G_{n,i,j}$ calculated. $R_{n,i,j}$ is a measure of the distance to critical structures and may be computed as:

$$R_{n,i,j} = \frac{\int_{E_{n,j}}^{T_{n,i}} d_{risk} - (f_{cri}(x) - d_{safe}) dx}{(d_{risk} - d_{safe}) * \text{length}} \quad \text{(Equation 2)}$$

where trajectories with $f_{cri}(x)$ closer than $d_{safe}$ have the highest risk ($R_{n,i,j}=1$), while $f_{cri}(x)$ greater than $d_{risk}$ have no risk ($R_{n,i,j}=0$). N.B. In Equation 2, length represents the length of the trajectory, i.e. the distance (or integral of xdx) between $T_{n,i}$ and $E_{n,j}$, while other terms used in Equation 2 are defined in Table 1 below.

$G_{n,i,j}$ measures the proportion of electrode contacts in GM. For each electrode, Q contacts with a recording radius of $p_r$ are spaced at even intervals $p_g$ along the trajectory. $G_{n,i,j}$ is calculated as:

$$G_{n,i,j} = \frac{\sum_{q=1}^{Q} H[f_{gm}(p_q - p_r)] + H[f_{gm}(p_q)] + H[f_{gm}(p_q + p_r)]}{3 * Q} \quad \text{(Equation 3)}$$

where $f_{gm}(\ )$ is the signed distance from the GM surface and H[ ] is the Heaviside function, with values of 1 inside GM and 0 outside. Each trajectory is assigned a weighted score $S_{n,i,j}$ computed as $S_{n,i,j}=10*R_{n,i,j}+G_{n,i,j}$, where the factor of 10 was determined empirically to that low risk is prioritized over a high GM ratio.

The final implantation plan V(N) is found by optimizing:

$$S_{total} = \operatorname*{argmin}_{V(n)} \left( \frac{1}{N} \sum_{n=1}^{N} S_{n,i,j} \right) \quad \text{(Equation 4)}$$

subject to $$D(\overline{T_{n,i}E_{n,j}}, \overline{T_{k,i}E_{k,j}}) > d_{traj} : \forall n,$$

$$\forall k \in \{1, \ldots, N\} n \neq k$$

where $d_{traj}$ specifies the minimum distance between trajectories that do not conflict. Due to the constraint $d_{traj}$, if the user selects multiple electrodes with the same ROI, ADMTP will find unique targets. For an implantation plan there are typically 7-12 electrodes, each with 1000-5000 potential trajectories (for example, representing approximately $10^{21}$ possible combinations. Therefore a depth-first graph strategy may be used to calculate a feasible implementation plan. If no combination of trajectories exists which satisfies $d_{traj}$, ADMTP returns the plan with the largest distance between trajectories.

It will be appreciated that the above approach for selecting a trajectory to one or more specified target locations is provided by way of example, and other known (or future developed) approach could be used—for example, the approach set out in WO 2015/173571 (as cited above), or as set out in certain of the References discussed above. The approach described herein is closely related to that set out in WO 2015/173571; for convenience, the latter is described in more detail section C below.

B) IMPLEMENTATION, EXPERIMENTAL DESIGN AND EXAMPLE RESULTS

FIG. 1 is a schematic block of the ADMTP system (tool) 100 for the pre-operative planning of electrode placement in accordance with some embodiments of the invention. The ADMTP tool 100 comprises application software 150 running on a (modern) computer workstation such as a personal computer (PC) 120 which is provided (inter alia) with an operating system 130, such as Mac OS X, Linux or Windows, at least one display 140, and a (modern) graphics card (graphics processing unit, GPU) 125 which functions as general-purpose parallel processor. The PC 120 will generally also be provided with standard components and accessories, such as a processor, memory (ROM/RAM), a hard disk drive, mouse, keyboard, etc, not explicitly shown in FIG. 1. The application software 150 generally runs on one or more processors provided within the computer workstation 120, but numerically intensive, parallel computations (such as determining the metric and/or assessing different trajectories) are off-loaded to the GPU 125 to increase overall speed. It will be appreciated that the configuration illustrated in FIG. 1 is provided by way of example only, and the skilled person will be aware of many other possible implementations on single computers (machines), distributed across two more computers, etc.

Figure 2A:
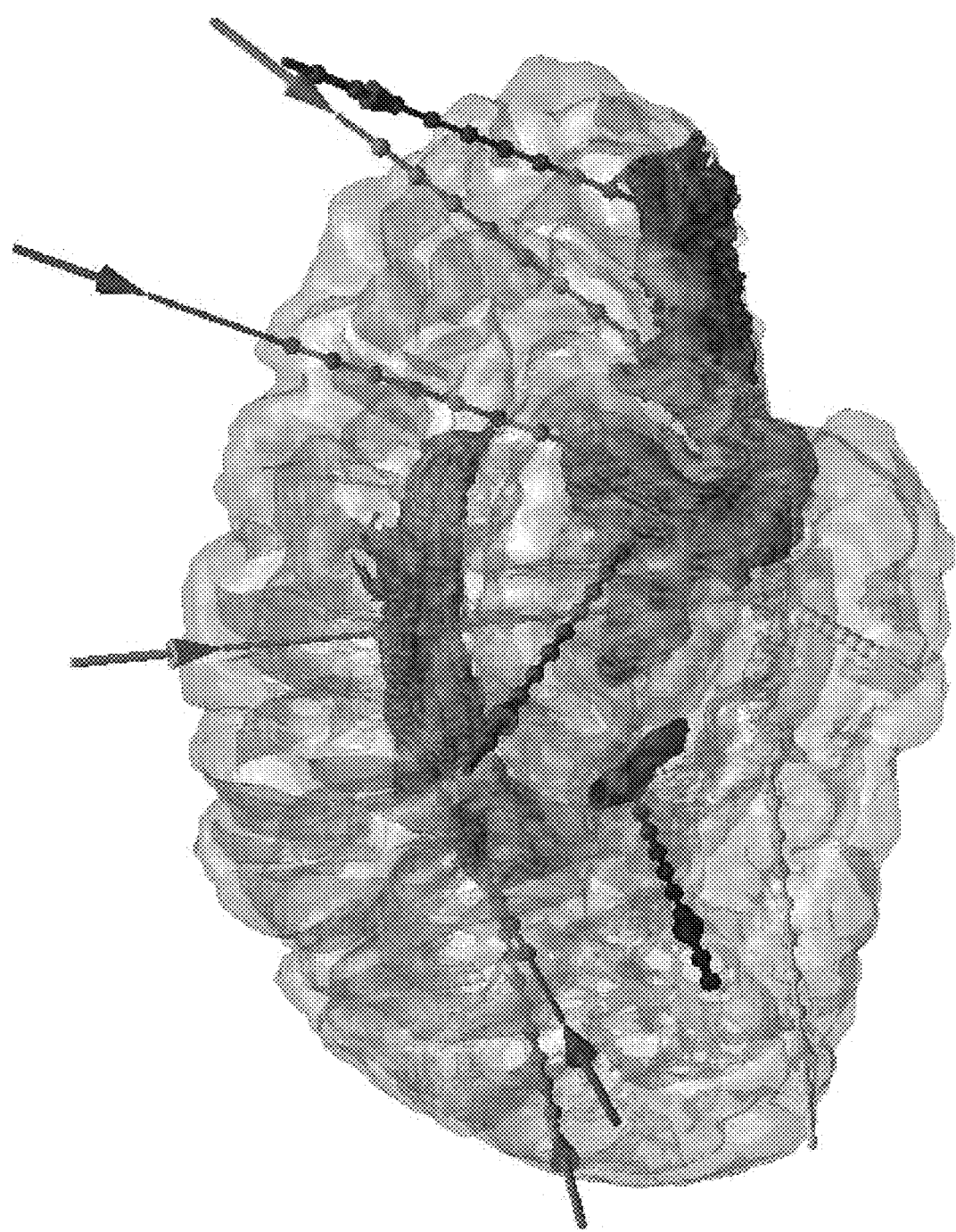
FIGS. 2A and 2B show examples of implantation plans for intra-cranial surgical insertions, with FIG. 2A highlighting deep ROIs and FIG. 2B highlighting superficial ROIs.
Figure 2B:
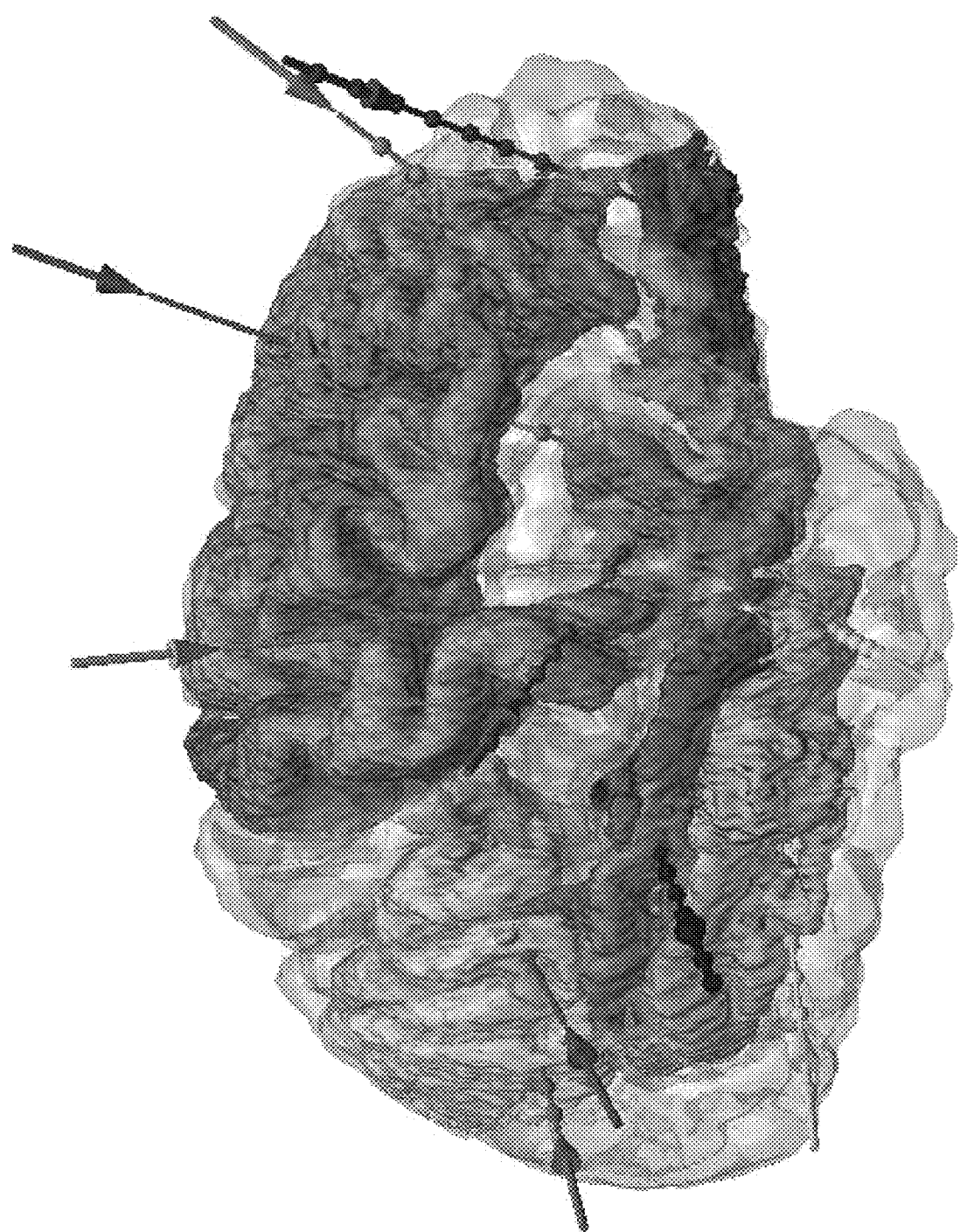

FIGS. 2A and 2B show an example of an implantation plan such as may be produced with the apparatus of FIG. 1. In particular, FIGS. 2A and 2B show an implantation plan with 10 electrodes. FIG. 2A shows the following deep ROIs: amygdala (cyan); hippocampus (yellow), anterior insula (brown), transverse temporal gyrus (blue), posterior (orange) and middle (purple) cingulate, posterior (green) and anterior (mauve) medial orbital gyrus. The electrodes are colour coded in accordance with the ROI into which they are implanted. Note that there is one electrode implanted into each ROI, except there are two electrodes implanted into each of the hippocampus and the anterior insula. FIG. 2B shows superficial ROIs, namely the middle frontal (blue), superior frontal (purple), middle temporal (light pink), and superior temporal (dark pink) lobes and supra-marginal (light orange), angular (light green) and precentral (dark green) gyri. The electrodes shown in FIG. 2B are the same as shown in FIG. 2B.

Figure 3A:
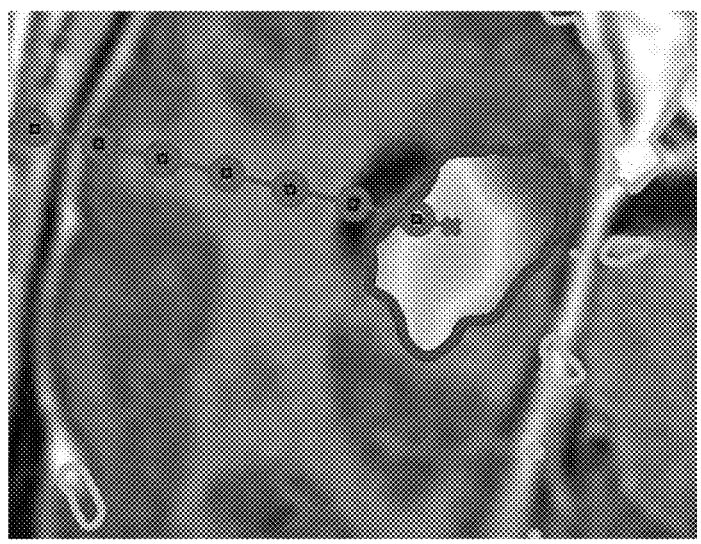
FIGS. 3A, 3B and 3C are axial, sagittal and coronal views respectively of the metric determined by the approach described herein for the hippocampus, and a trajectory selected by the approach described herein.
Figure 3B:
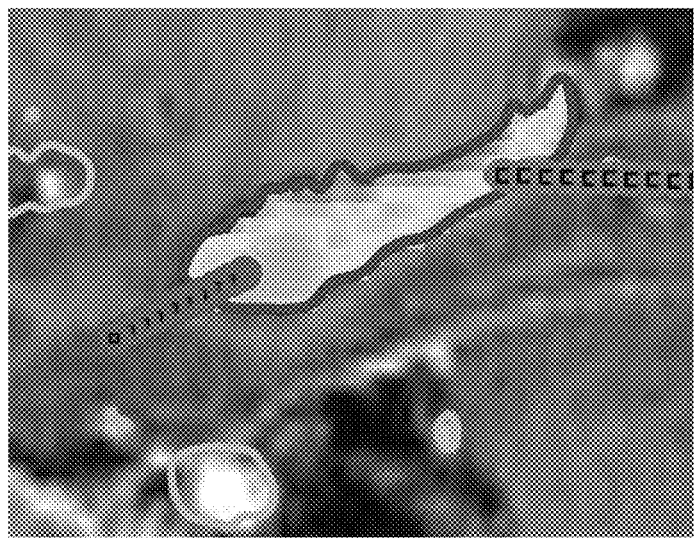
Figure 3C:
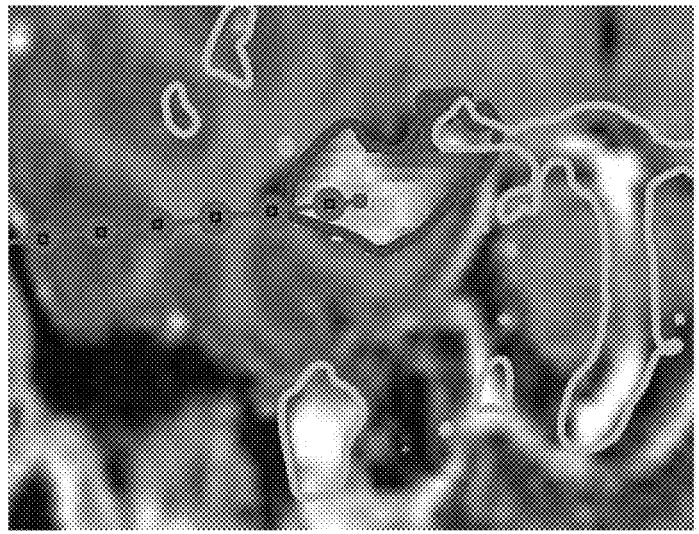
Figure 4B:
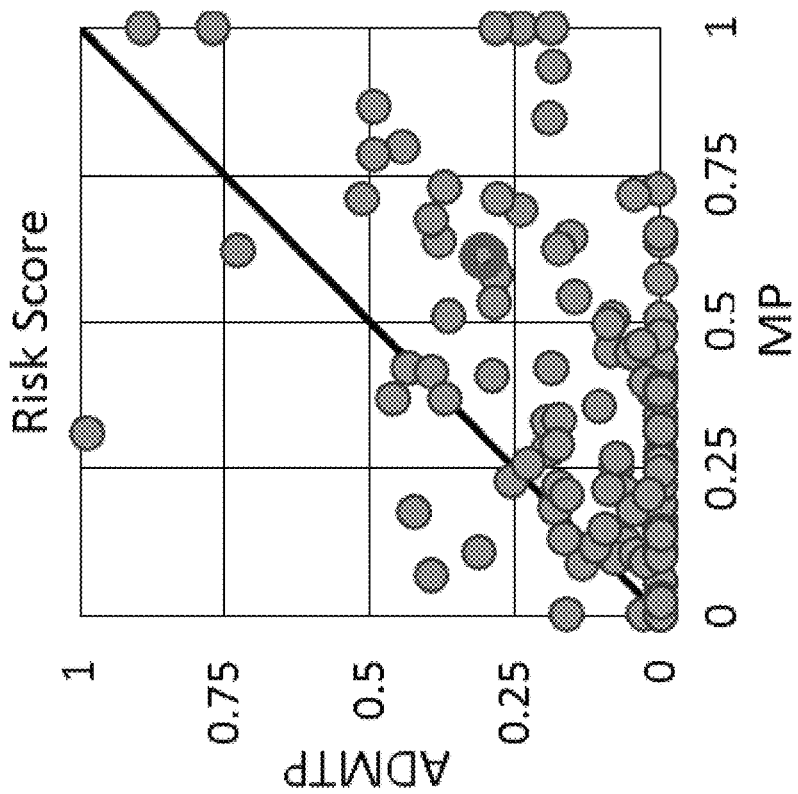
FIGS. 4A-4D are graphs comparing the suitability of trajectories determined by the approach described herein with trajectories determined by manual planning.
Figure 4A:
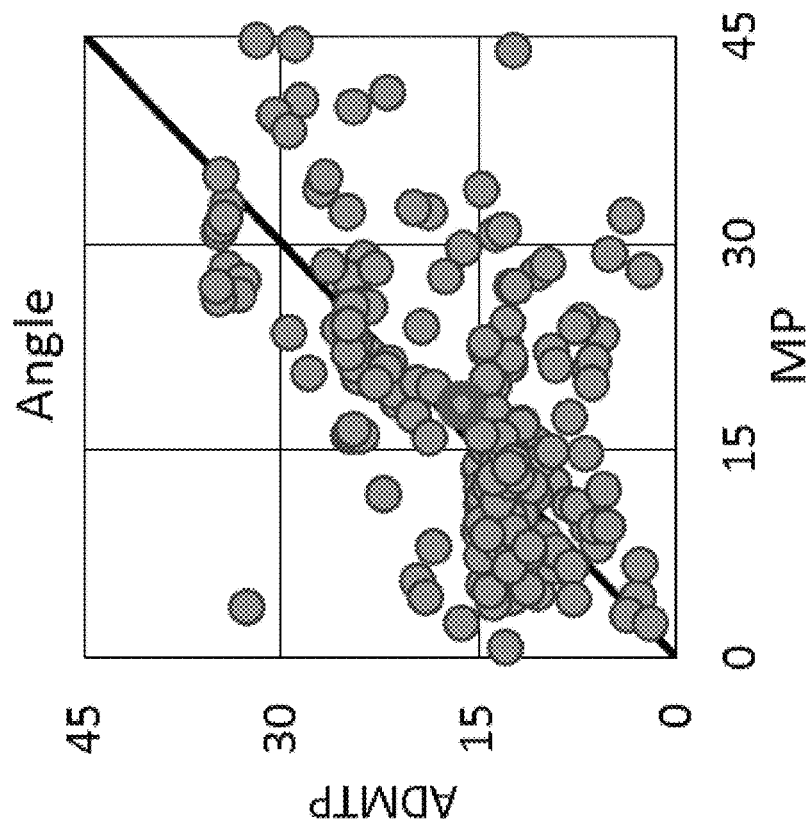
Figures 4C, 4D:
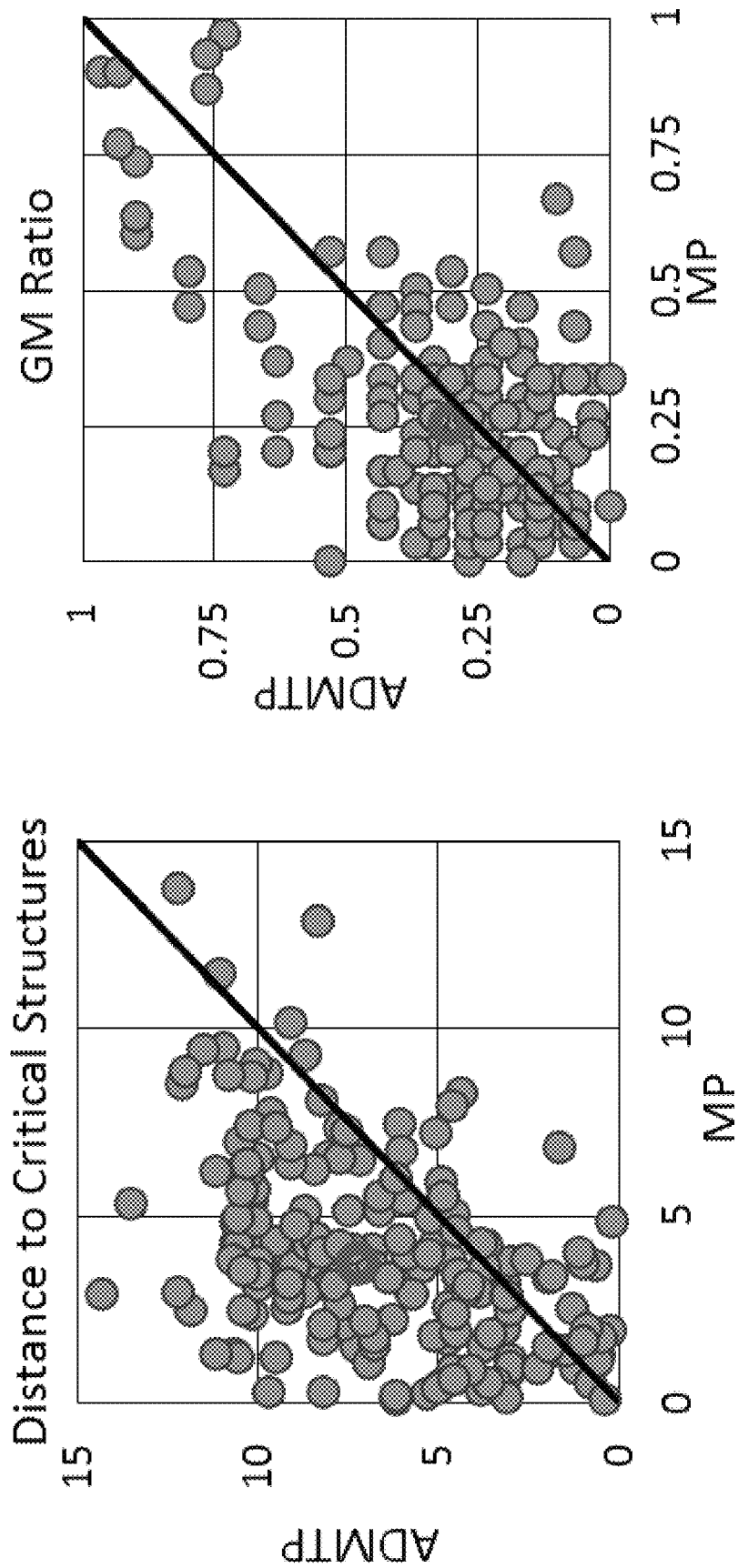

FIGS. 3A, 3B and 3C show an example of axial (FIG. 3A), sagittal (FIG. 3B) and coronal (FIG. 3C) views of $C_t$ (the target risk image) for the hippocampus (outlined in dark blue). In particular, the hippocampus is coloured in the form of a heat map of the metric $f_t(c)$, where red indicates a high value of the metric (low suitability), and green indicates a low value of the metric (high suitability). FIGS. 3A, 3B and 3C also show blood vessels (cyan) to be avoided, and various trajectories determined by ADMTP according to the approach described herein.

In one particular experiment, the ADMTP tool has been evaluated using retrospective data from 20 patients with medically refractory epilepsy who underwent intracerebral implantation. Patients had between 7 to 12 electrodes per plan for a total of 186 electrodes. Manuals plans (MP) were determined by the consensus of two neurosurgeons using manual inspection. Deep and superficial ROIs were identified by the same two neurosurgeons. The parameters used by the ADMTP tool for this evaluation are as set out in Table 1 (the values of Table 1 are provided by way of example only, and it will be appreciated that other implementations may adopt different values).

TABLE 1 examples of parameters used for the approach described herein. The first four values in the table were determined empirically, the remainder based on the consensus of 3 neurosurgeons.

| Parameter | Value |
|---|---|
| M (number of candidate targets) | 10 |
| $d_{tar}$ (minimum distance between candidate targets) | 3 mm |
| $\omega_{roi}$ (relative importance for depth in region of interest) | 0.25 |
| $\omega_{cri}$ (relative important for distance from critical object) | 0.75 |
| $d_{len}$ (length threshold above which trajectories are excluded from consideration) | 80 mm |
| $d_{ang}$ (the most oblique entry angle permitted) | 25 degrees |
| $d_{safe}$ (the minimum safe distance from a blood vessel) | 3 mm |
| $d_{risk}$ (the distance at which there is no risk) | 10 mm |
| Q (the number of contacts per electrode) | 10 |
| $p_q$ (the interval between contacts) | 6 mm |
| $p_r$ (the contact sample radius) | 1.2 mm |
| $d_{traj}$ | 10 mm |

As illustrated in FIGS. 4A-4D, electrode trajectories were assessed for suitability on 4 quantitative measures: (a) angle with respect to the skull normal, (b) risk score, (c) distance to the nearest critical structure, and (d) grey matter ratio. Red circles are used to indicate the centre of mass for each measure. For each plot of FIGS. 4A-4D, the trajectory values are depicted such that each point corresponds to a single trajectory with the MP value plotted on the X axis and the ADMTP value plotted on the Y axis. For FIGS. 4A and 4B, points below the diagonal correspond to ADMTP giving the preferred result; for FIGS. 4C and 4D, points above the diagonal correspond to ADMTP giving the preferred result;

A two-tailed Student's t-test was used to test the statistical significance between trajectory values determined by ADMTP and MP with the null hypothesis being that the two methods return similar values. ADMTP was found to reduce the angle in 96/186 trajectories (p=0.070), increased the grey matter ratio in 104/186 trajectories (p=0.012), reduced the disk score in 145/186 trajectories (p=4.8×10$^{-14}$), and increased the distance to the closest critical structure in 145/186 trajectories (p=1.1×10$^{-16}$). In general terms, ADMTP was therefore able to find trajectories that are safer, in terms of larger distances to blood vessels, compared to MP.

The plans were further assessed based on (1) distance between trajectories (to avoid interference), and (2) the ratio of gyri sampled to total electrodes (which can be considered as a measure of efficiency)—a ratio of 1 corresponds to each electrode targeting a unique gyri. In the above evaluation, ADMP was found to provide an average distance between trajectories of 38.3 mm (5.2-124.2 mm) compared to MP with an average of 36.37 mm (1.28-117.47 mm). MP and ADMTP both have 12 electrode pairs under the $d_{traj}$ of 10 mm (see Table 1). MP provided an average gyri to electrode ratio of 0.96 (0.86-1) while ADMTP provided a ratio of 0.92 (0.75-1). Thus although ADMTP has larger distances between trajectories, MP provides better coverage in terms of more unique gyri sampled and more consistent coverage of the cortex.

The computational efficiency of ADMTP was assessed for computing candidate target points, trajectories, and ADMTP (the combination of both steps). Computations were performed on a computer, generally corresponding to the system 120 shown in FIG. 1, which included an Intel Xeon 12 core CPU and speed of 2.10 GHz with 64 GB of RAM and a single NVIDIA Quadro K4000 4 GB GPU. The computation times using this platform are shown in Table 2 below—ADMTP took 61.14 seconds (15.43-279.20 seconds) with most of the computation time spent on trajectory planning. (To put these timings into perspective, manual planning of multiple trajectories by visual inspection typically takes 2-3 hours).

TABLE 2 computation timings, in seconds, for candidate target point selection, trajectory planning, and ADMTP

| Algorithm | Median Time (range) in seconds |
| --- | --- |
| Target point selection | 6.91 (3.5-19.18) |
| Trajectory planning | 54.07 (7.86-264.01) |
| ADMTP | 61.14 (15.43-279.20) |

Figure 5A:
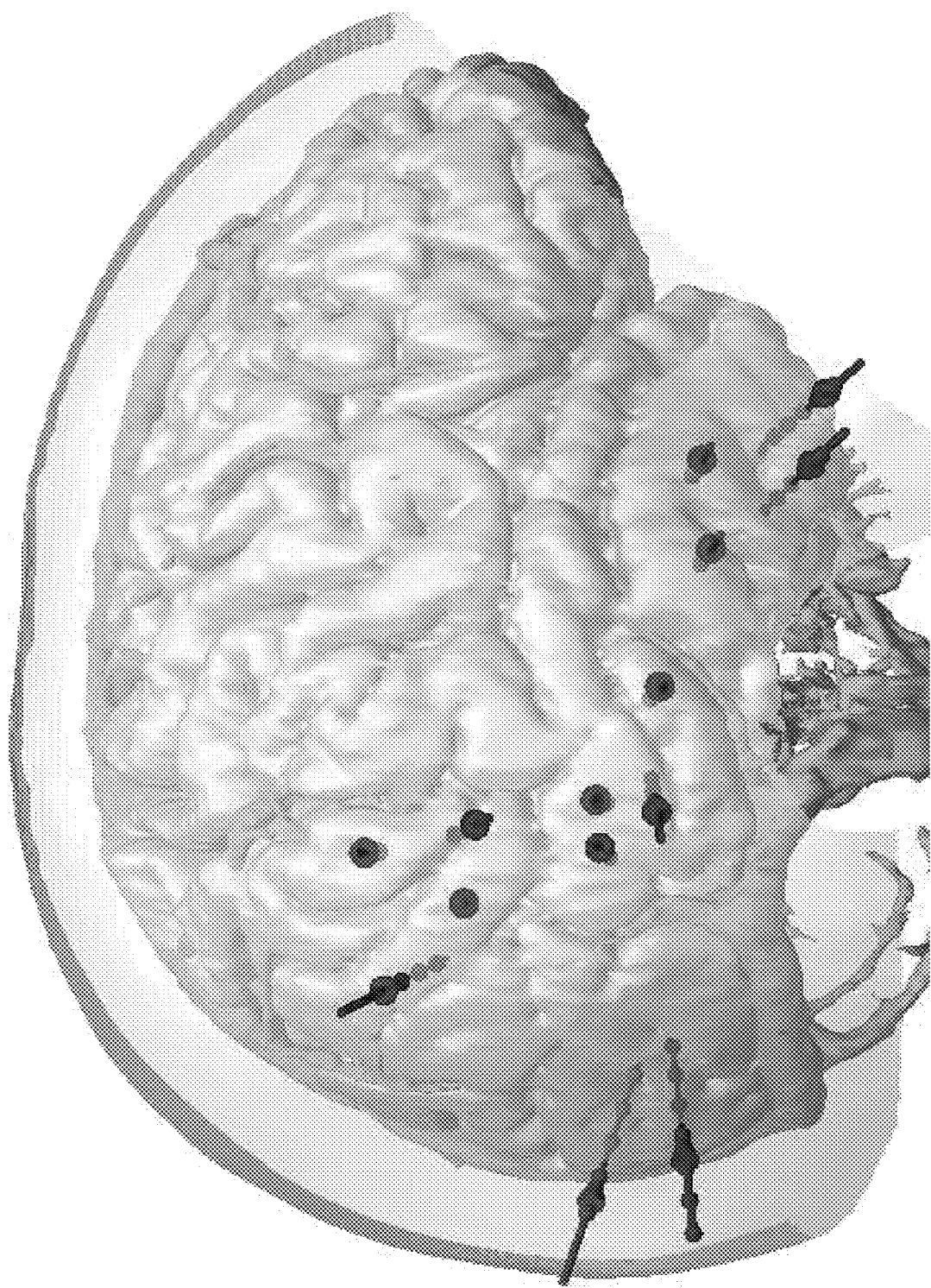
FIGS. 5A and 5B show for comparison trajectories determined by the approach described herein and trajectories determined by manual planning, with FIG. 5A including the cortex and FIG. 5B excluding the cortex.
Figure 5B:
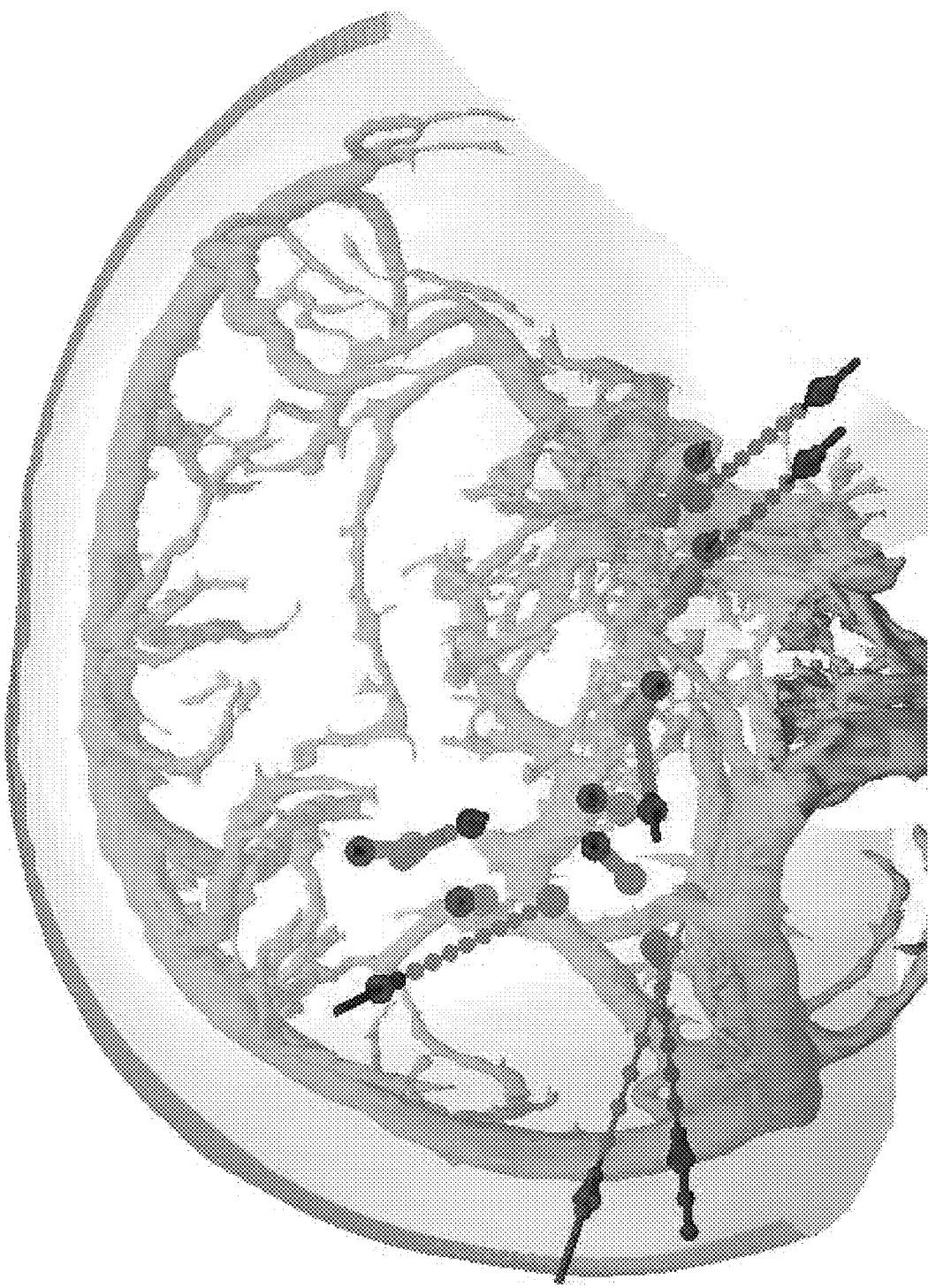

FIGS. 5A and 5B shows some results from the above experiment, in particular with the manual plan shown in pink, and the ADMTP plan shown in blue (the skull is shown in opaque white, and the cortex in peach). FIG. 5B shows target point differences within the cortex, while FIG. 5A shows entry point differences. ADMTP often found trajectories within the same gryus as manual planning.

C) TRAJECTORY SEARCHING

As mentioned above, WO 2015/173571 discloses an approach for searching for entry points and performing a trajectory risk analysis. This approach may be used for selecting a trajectory to a set of one or more target locations such as found using the methodology described in section A above. The approach of WO 2015/173571 will now be described to provide additional information as regards (i) entry point selection, (ii) determining the risk factor and other suitability measures associated with a given proposed trajectory, and (iii) accommodating the presence of multiple electrodes so that trajectories for respective electrodes do not interfere with one another. The techniques set out below are broadly similar to those already described in section A above, but contain additional details and minor variations. Accordingly, the following description provides additional information and alternatives for implementing the techniques already described in section A above for identifying, assessing and selecting the trajectories to the potential target locations (and ultimately to the deep ROIs).

After the potential target locations have been selected (see section A above), the entry points can be selected manually by the user and/or automatically by the system 100. An entry point can only be placed onto the skull surface (a 3D representation of the skull surface is derived from the input images). The system 100 is able to analyse automatically the topology of the critical structures and to offer a set of potential entry points that represent minimal risk. This entry point search is a fully automated method that is implemented on the GPU 125. The method takes the mesh representation of the skull surface as the input and processes each vertex of the index, so that the sampling space and rate when searching for possible entry points are defined by the number and location of vertices in the skull model. The risk associated with each potential trajectory (from a potential entry point to the target point) is evaluated in real-time using the GPU 125, and unsuitable (e.g. high risk) candidates are ruled out.

An entry point search is performed to find the set of potential entry points that represent minimal risk. The first portion of this search involves a proximity search to find all points on the skull surface which are within a predetermined distance of the target point, where the predetermined distance reflects a maximum length for a trajectory. This maximum length may in turn be specified based on the physical characteristics and/or operational requirements of the electrodes that are being inserted.

The entry point candidates from the proximity search are then analysed to find the angle of entry by computing the deviation between the direction vector of the trajectory and the surface normal of the skull at the point of entry. From a practical (surgical) point of view the entry angle should be as close to perpendicular as possible, otherwise it becomes increasingly difficult to drill the keyhole through the skull. Therefore, if the entry angle of an entry point is outside a user-configured range (e.g. more than 10 or perhaps 20 degrees from perpendicular), the entry point is ruled out.

Since the analysis of trajectory length and entry angle is computationally inexpensive, it is feasible to perform such analysis for all possible entry points (i.e. for all nodes or vertices of the surface mesh) and then to disqualify (filter out) those entry points for which the trajectory is too long (greater than some threshold) or the entry point angle is too great (further from the perpendicular than some threshold angle, such as 10 degrees). Each of the remaining entry point candidates, i.e. which are suitably close to the target point and have an acceptable entry angle, is then checked for any collision with the critical structures. If the position of an entry point does not allow straight access to the target point without collision with any critical structure, it is disqualified from the further analysis. This evaluation procedure further reduces the number of candidate entry points.

The above filtering of entry point candidates significantly reduces the number of remaining entry point candidates (compared with the original number of entry point candidates), thereby permitting a more detailed, automated, risk analysis of the remaining entry point candidates while still maintaining real-time and interactive performance. Note that previously published risk metrics have generally assigned risk based on the shortest Euclidean distance to a critical object from any point on the trajectory. In contrast, the metric used for the present approach is based on a cumulative risk profile which may be obtained along the full length of the trajectory.

The automated risk analysis starts by investigating the distance from each trajectory to the critical structures. For each potential trajectory from a candidate entry point to the target point (target location), a predetermined number of sample locations are considered along the length of the trajectory. (In the current implementation, the predetermined number of sample locations is 256, but other implementations may use a smaller or larger number, and/or may make this number configurable by the user).

The system 100 now calculates, for each sample point, the minimum distance to the critical structures (one at a time). The minimum distance to the nearest critical object for that sample point, which is referred to as the critical distance, is then recorded in an array which lists, for each sample point along the trajectory, the corresponding critical distance.

Once the critical distances have been identified for each potential trajectory, an overall risk computation is performed using a new integrative risk metric that quantifies the level of risk on a 0-1 scale (0—no risk; 1—the highest risk which must be avoided). This metric can be extended, if so desired, to include one or more additional factors as discussed above, such as distance and angle of entry, as well as whether the electrode contacts are in grey matter.

A trajectory is considered too risky if the minimum distance to any critical structure, for any sample point on that trajectory, is less than a preset distance: $d_{min}$, which can be considered as defining a safety margin. Conversely, if all sample points on a trajectory lie further from a critical structure than a distance $d_{max}$, which can be considered as defining the boundaries of a risk zone, then the critical structure represents no potential harm to the trajectory. Note that the values of $d_{min}$ and $d_{max}$ can be configured by the user as required in the system.

We can therefore quantify the overall level of risk arising from proximity to critical structures or objects according to the following:

$$R_{dist} = 1/L \int_{entry}^{target} f(d(x) - d_{min}) dx \qquad (Eq\ 5)$$

where x represents the distance along the trajectory to a given sample point, L represents the total distance from entry to target (i.e. the integral of dx from entry to target) d(x) represents the critical distance for the sample point at distance x, and f(y) is a function which decreases monotonically from f (y)=1 at y=0 to f (y)=0 at $y \geq d_{max} - d_{min}$. Note that:

a) f(y) may be specified to have a simple straight line shape, or may have some other form if this better represents the variation in risk with critical distance;

b) for y<0, f (y) can be considered as undefined, or infinite. This value for y (which represents $d(x) < d_{min}$), would imply that the critical distance at this sample point is less than the safety margin, $d_{min}$, and hence this trajectory should be eliminated;

c) Equation 5 yields a value for $R_{dist}$ which is in the range of 0-1; and d) Equation 5 is presented as an integral, which in effect assumes a continuous (infinite) distribution of sample points along the trajectory, but it can be readily converted into a summation for a finite number of sample points.

The (predicted) risk associated with (emanating from) the entry angle can be similarly expressed as a risk, $R_{angle}$, based on the range of accepted values, likewise the risk associated with (emanating from) the length of the trajectory: $R_{length}$. For example, an offset angle from the perpendicular of 0 degrees may be assigned a risk of 0, while an offset of (e.g.) 10 degrees may be assigned a risk of 1 (entry points with a higher offset angle would have already been eliminated); intermediate offset angles are then assigned an appropriate intermediate risk value. An analogous approach can be used to assign a risk to the trajectory length.

These independent risk components can be combined by applying appropriate weighting factors (w) to give a total or overall risk:

$$R_{total} = w_1 R_{dist} + w_2 R_{angle} + w_3 R_{length} \qquad (Eq\ 6)$$

where $\Sigma w_i = 1$ and $R_i \in [0\sim 1]$

This final metric $R_{total}$, which has a value between 0 (lowest risk) and 1 (highest risk) describes the overall quality of (risk associated with) a given trajectory. (The risk can also be regarded as a form of cost function, where a low risk or cost is desirable).

For the system 100, the risk evaluation is performed on the GPU 125. To assist the proximity search and distance evaluations in completing in real-time, a Bounding Volume Hierarchy (BVH) is built over the triangle vertices or cells of critical structures. A BVH is an acceleration data structure that allows the fast traversal of large datasets containing 3D points.

In some implementations, the system 100 further includes a risk analysis module which is used to perform real time analysis of critical distances, entry angle (as above) and grey matter/white matter ratio. This latter parameter is significant, since it is generally desired to place the electrodes used for SSEG in grey matter (for clinical reasons to best detect the desired signals). In addition, a typical electrode may in practice have multiple contacts which are spaced along the length of the trajectory. Having a high grey matter/white matter ratio improves the likelihood that these electrode contacts are situated in grey matter (as desired) rather than in white matter. If this ratio is below a configurable threshold, the user may be warned to re-consider the placement.

It will be appreciated that there are other ways of determining a risk or cost associated with grey matter/white matter. For example, if the particular number and location of the contacts on a given electrode are known (e.g. based on manufacturer specifications), then it can be determined how many (or what fraction) of the contacts are located in grey matter for a given trajectory, and then set the cost or risk accordingly.

As described above, the risk analysis is performed automatically to determine a final metric $R_{total}$ that describes the overall quality of any given trajectory. More particularly, this metric can be determined for a large number of potential trajectories. Safe zones and no-go areas can be derived as appropriate.

After the associated risks have been computed and the quality of all the potential trajectories has been assessed, the risk values may be visualized. The system 100 is provided with a display 140 which is used to present a visualization of risk. For example, the system 100 supports a colour coded display of the associated critical distance to each sample point along the trajectory.

In many practical applications, it is generally desired to implant multiple electrodes. These electrodes should not interfere with one another. Accordingly, the placement of each entry point should also take into consideration the placement of the other entry points (for other target locations). One way of achieving this is to determine an entry point using the above approach for each target point in turn. Trajectories that have already been determined for previous target points can then be treated as critical structures to be avoided (as for the other critical structures), as each new trajectory is determined. Although this approach is feasible, it is dependent on the ordering in which the target points are chosen for determining a trajectory, and may therefore not provide the best overall solution. The system 100 therefore incorporates a multiple trajectory planning process which avoids such sensitivity on target point ordering. The process starts with the user selecting the desired set of N target points $T_i$: $i \in \{1, \ldots, N\}$. For each target point in this set, the entry point search and risk analysis procedure is run independently to obtain a set of M potential entry points $E_{i,j}$: $j \in \{1, \ldots, M\}$—i.e. entry points that are not excluded or filtered out by virtue of being too long, having an unacceptable entry angle, or going directly through a critical structure to get to the target point. Each potential target/entry point pair in a set M is represented by a trajectory $\overline{T_iE_{i,j}}$. The risk analysis procedure described above then returns a risk score $R_{i,j}$ that describes the overall quality for each $\overline{T_iE_{i,j}}$ trajectory in M (note $R_{i,j}$ corresponds to $R_{total}$ in Equation (6) above).

The multiple trajectory planning procedure seeks to find an optimal combination of trajectories for all of the N target points such that they do not interfere with one other. Trajectory interference is considered to occur if the minimum distance between any two trajectories is smaller than a "Trajectory Margin" distance: $d_{min}$. This trajectory margin distance can be configured by the user, and may be set as appropriate to be the same as, or different from, the $d_{min}$ used to specify the safety margin around the critical structures.

The optimal combination of N trajectories can then be calculated as a combination of the risk scores for each trajectory:

$$R_{all} = \min_{R_{all}} \frac{1}{N} \sum_{i=1}^{N} R_{i,j} : j \in \{1, \ldots, M\} \quad \text{Equation (7)}$$

subject to $D(\overline{T_iE_{i,j}}, \overline{T_kE_{k,j}}) > d_{min}$: $\forall i \in \{1, \ldots, N\}$, $\forall k \in \{1, \ldots, N\}$, $i \neq k$. Note that $D(\overline{T_iE_{i,j}}, \overline{T_kE_{k,j}})$ represents the minimum distance between the two trajectories $\overline{T_iE_{i,j}}$ and $\overline{T_kE_{k,j}}$. The final metric $R_{all}$ describes the overall quality (risk or cost) of the trajectory combination on a 0-1 scale (0—no risk; 1—the highest risk which must be avoided).

To support real-time optimization of $R_{all}$, a dynamic programming depth-first search algorithm is utilized. The algorithm starts with an initial value of n=1, and proceeds as follows:
1) Find the combination of n trajectories having the (next) lowest risk score.
2) Evaluate if $D(\overline{T_iE_{i,j}}, \overline{T_kE_{k,j}}) > d_{min}$ for all n trajectories.
3) If false return to (1); if true find the next lowest risk score for n+1 trajectories (and increment n).
4) Return when a valid configuration for n=N is found.

In this approach, the target points or trajectories are effectively added in one at a time. For n=1, step 1 is simple, it just involves selecting the trajectory for that target location which has the lowest overall risk factor (on an individual basis). For n=1, step 2 necessarily returns true (because a single trajectory cannot have a conflict with itself). We therefore return to step 1, and include the trajectory for a second target point, in particular the trajectory which has the lowest overall risk factor (on an individual basis) for this second target point. However, if a conflict is found at step 2, i.e. the distance between the new trajectory and the existing (already included) trajectory is less than $d_{min}$, then selected entry points are reconsidered at step 1 for both of the target points (not just the newly added target point) to find the (next) lowest combination of risk factors for the two target locations. This procedure is then repeated, adding in another target location at a time, until all N trajectories have been determined. Note that by considering only the lowest valid combination of trajectories at step 1 of each iteration, the output of this algorithm produces the optimal (in terms of risk score minimization) configuration of electrodes.

D) FLOWCHART

The present approach provides a method of using a computer system to assist in planning a trajectory for a surgical insertion into a skull to a target representing an anatomical region, as well as an apparatus and computer program for implementing such a method.

Figure 6:
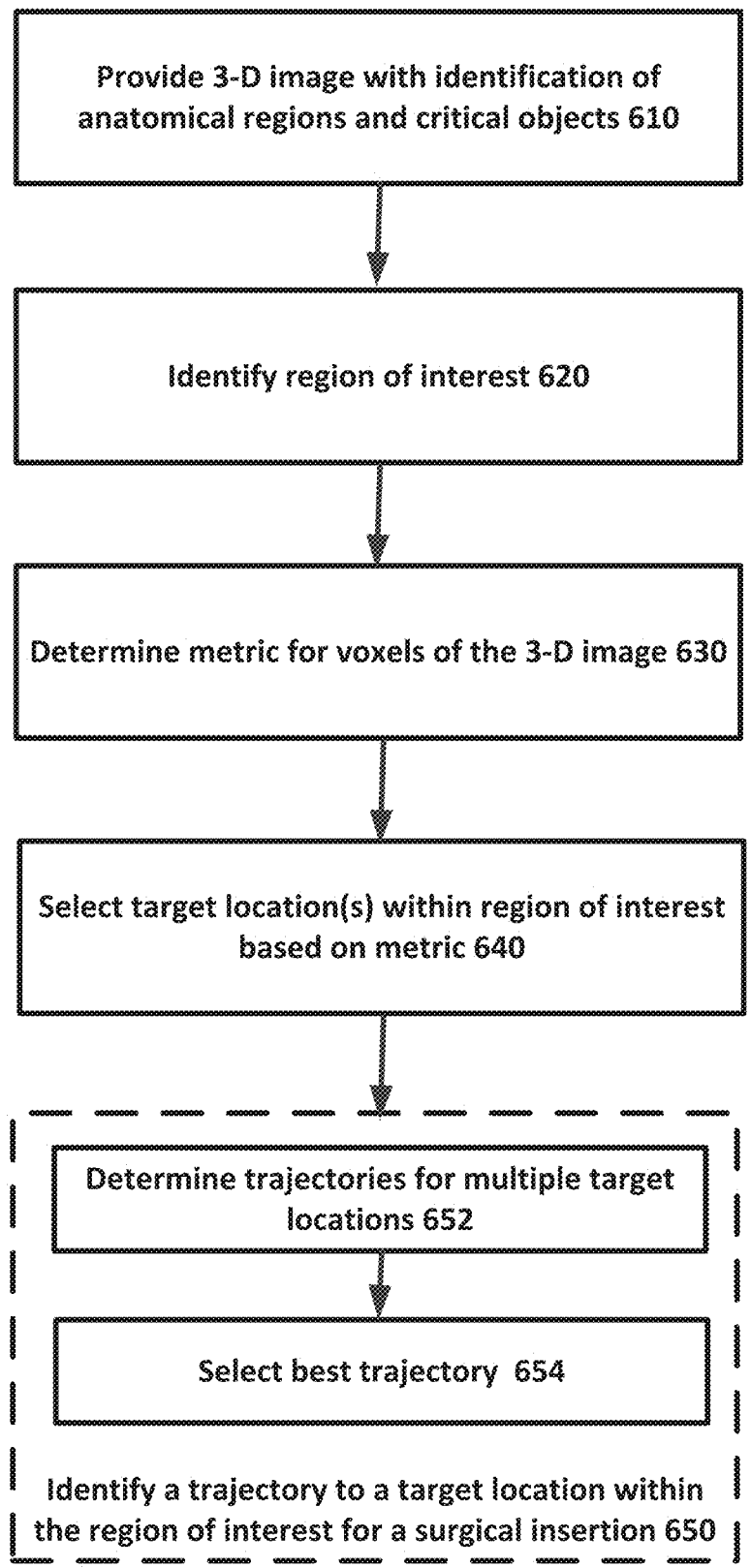
FIG. 6 is a flowchart showing the approach described herein for determining a trajectory for a surgical insertion.

FIG. 6 shows a high-level flowchart corresponding to this method, which begins with providing the computer system with a three-dimensional image representation of the skull and brain which has been parcellated into anatomical regions (610). For example, the image may comprise a set of voxels (pixels in 3D space) with each voxel labelled according to the anatomical region in which the voxel is located. Thus the image is formed of voxels, each voxel representing a spatial coordinate with an associated label indicating the anatomical region at that spatial coordinate. However, the image representation may be provided in alternative formats. For example, the image representation may be provided as a listing of anatomical regions, with each region being named, and provided with a geometrical expression or model (e.g. mesh) defining the surface of the region.

Furthermore, the computer system is provided with an identification of critical objects comprising structures within the skull to be avoided during the surgical insertion. This identification includes the location of the critical objects within the three-dimensional representation. The three-dimensional image representation and critical object segmentation can generally be obtained from CT and/or MR imaging (for example).

A user also provides the computer system with one or more regions of interest (620), each region of interest corresponding to an anatomical region within the skull representing the target of the trajectory for the surgical insertion. For example, the user may provide the labels associated with the anatomical region, such that they can be found by the system in the three-dimensional image representation.

The system now determines a metric for voxel locations within the anatomical region(s) corresponding to the region of interest(s) (630). The metric represents the suitability of each of the voxel locations to be a target location for the trajectory for a surgical insertion. (In the following discussion, we assume a high value of the metric represents a good suitability, but it will be appreciated that in some implementations, a good suitability might be represented by a low value of the metric). In some cases, the metric may be calculated for each voxel in a region of interest, in other cases, the metric may be determined for only a subset of the voxels (e.g. every other voxel) to reduce processing costs. A further possibility is that the voxel locations are specified as a separate set of spatial coordinates (e.g. a grid) which can be mapped onto the region of interest in the three-dimensional image representation.

For each region of interest, a set of one or more voxel locations having the greatest (or good) suitability according to the metric is selected (640). Each of the one or more selected voxel locations represents a potential target location for the trajectory. The system then identifies a trajectory to a potential target location in the region of interest which can be used for the surgical insertion (step 650).

In many practical implementations, multiple potential target locations are identified within a region of interest—for example, corresponding to local maxima of the metric within the region of interest. Identifying a trajectory for the surgical insertion may then comprise determining one or more trajectories to each of the multiple potential target locations (652), and then selecting the best of these trajectories (654), for example based on lowest risk factor (and any other relevant factors, e.g. GM sampling), to use for the surgical insertion to the region of interest. In some cases, multiple trajectories are determined at operation 652 to each of the potential target locations. At operation 654, the best trajectory for each potential target location is first determined (according to criteria discussed above), and then the best overall trajectory for the region of interest is identified from the best trajectories for each potential target location.

Accordingly, it will be appreciated that there are many different implementations according to circumstances. For example, in some cases, the metric might be used to determine a single target location within a region of interest (e.g. representing a maximum value of the metric within the region of interest). The system then determines a trajectory for the surgical insertion to this single target location. In the event that no suitable trajectory can be found, the system may then identify a second potential target location (e.g. based on a subsidiary or neighbouring peak of the metric), and try to find a good trajectory to this second potential target location. In other cases, the metric might be used to determine multiple potential target locations, and corresponding (best) trajectories are determined for each potential target location. This latter approach may give a more suitable trajectory for the surgical insertion, in that the best trajectory overall to a given region of interest may not necessarily terminate at the most suitable target location. In addition, in some cases, e.g. for a large region of interest, two (or more) electrodes might be inserted into the same region of interest, and these can use different potential target locations for the different electrodes.

The metric is generally independent of any trajectory leading to the voxel location for which the metric is being calculated. For example, the metric may be based on distance from the nearest critical objects, such that the suitability of a voxel location increases with distance from the nearest surface of the critical objects, and/or on distance inside the region of interest, such that the suitability of a voxel location increases with distance inside the region of interest. This allows the metric to be calculated relatively quickly (e.g. because there is no set of calculations to be repeated at each location along the path of a trajectory).

A potential target location can be identified as a maximum (or local maximum) of the metric using any suitable approach, e.g. a hill-climbing algorithm, subject to the accuracy of the maximum finding technique. For example, in some cases the analysis may not locate the precise maximum, but rather identify a location having a relatively high value—e.g. in the vicinity or neighbouring to the precise maximum. For present purposes, a relatively high value of the metric (compared to surrounding or all other voxels) will be considered as representing locations having the greatest suitability according to the metric.

If multiple potential target locations are being located within a given region of interest, the assessment of suitability may take into consideration the distance between the potential target locations—if they are very close together, this in effect reduces the spread of trajectories to the region of interest that will subsequently be considered. Accordingly, the system may, for example, impose a constraint on selecting the set of one or more voxel locations to represent potential target locations, the constraint requiring a predetermined minimum distance between the potential target locations within the region of interest. This can improve robustness in finding a good trajectory to the region of interest by considering a wider spread of trajectories. The number of potential target locations to select within a given region of interest depends upon the particular circumstances (including clinical need), but may for example fall in the range 5 to 25, e.g. preferably 8 to 15.

In many implementations, a user will select multiple regions of interest, and a respective trajectory will then be identified for each region of interest. This identification may be performed in a similar manner to the approach set out above for a single region of interest, usually with the added constraint that the trajectories for different electrodes (e.g. to different regions of interest) must not conflict.

E) CONCLUSION

Compared to manual planning, the use of ADMTP as described here has been found to lower risk for 76% of trajectories and to increase GM sampling in 56% of trajectories (according to the experimental results obtained above). In addition, ADMTP is relatively inexpensive in computational terms, such that trajectories can be determined in real-time (or at least near real-time). This suggests that ADMTP is a feasible and potentially valuable tool for use in computer-assisted planning of one or more trajectories for surgical insertion into a skull.

Various embodiments of the invention have been described above. The skilled person will appreciated that the features of these embodiments may be combined with one another as appropriate, or modified according to the particular circumstances of any given application. The scope of the invention is defined by the appended claims and their equivalents.

REFERENCES

1. Beare, R., Lehmann, G.: Finding regional extrema—methods and performance (2005), http://hdl.handle.net/1926/153
2. B'eriault, S., Subaie, F. A., Collins, D. L., Sadikot, A. F., Pike, G. B.: A multi-modal approach to computer-assisted deep brain stimulation trajectory planning. IJCARS 7(5), 687-704 (2012)
3. Cardoso, M. J., Modat, M., Wolz, R., Melbourne, A., Cash, D., Rueckert, D., Ourselin, S.: Geodesic information flows: Spatially-variant graphs and their application to segmentation and fusion. IEEE TMI 34(9), 1976-1988 (2015)
4. De Momi, E., Caborni, C., Cardinale, F., Casaceli, G., Castana, L., Cossu, M., Mai, R., Gozzo, F., Francione, S., Tassi, L., Lo Russo, G., Antiga, L., Ferrigno, G.: Multi-trajectories automatic planner for StereoElectroEncephaloGraphy (SEEG). IJCARS pp. 1-11 (2014)
5. Essert, C., Haegelen, C., Lalys, F., Abadie, A., Jannin, P.: Automatic computation of electrode trajectories for Deep Brain Stimulation: a hybrid symbolic and numerical approach. IJCARS 7(4), 517-532 (2012)
6. Shamir, R. R., Joskowicz, L., Tamir, I., Dabool, E., Pertman, L., Ben-Ami, A., Shoshan, Y.: Reduced risk trajectory planning in image-guided keyhole neuro-surgery. Medical Physics 39(5), 2885-2895 (2012)
7. Zelmann, R., Beriault, S., Marinho, M. M., Mok, K., Hall, J. A., Guizard, N., Haegelen, C., Olivier, A., Pike, G. B., Collins, D. L.: Improving recorded volume in mesial temporal lobe by optimizing stereotactic intracranial electrode implantation planning. IJCARS 10(10), 1599-1615 (2015)
8. Zombori, G., Rodionov, R., Nowell, M., Zuluaga, M. A., Clarkson, M. J., Micallef, C., Diehl, B., Wehner, T., Miserochi, A., McEvoy, A. W., Duncan, J. S., Ourselin, S.: A computer assisted planning system for the placement of seeg electrodes in the treatment of epilepsy. In: IPCAI 2014, Lecture Notes in Computer Science, vol. 8498, pp. 118-127. Springer International Publishing (2014)
9. Zuluaga, M. A., Rodionov, R., Nowell, M., Achhala, S., Zombori, G., Mendelson, A. F., Cardoso, M. J., Miserocchi, A., McEvoy, A. W., Duncan, J. S., Ourselin, S.: Stability, structure and scale: improvements in multimodal vessel extraction for seeg trajectory planning. IJCARS 10(8), 1227-1237 (2015)
10. Duncan, J. S.: Imaging in the surgical treatment of epilepsy. Na Rev Neurol 6(10), 537-550 (October 2010)
11. Klein, A., Tourville, J.: 101 labeled brain images and a consistent human cortical labeling protocol. Frontiers in Neuroscience 6(171) (2012)
12. Hartigan J A, Wong M A (1979) Algorithm AS 136: A k-means clustering algorithm. J R Stat Soc Ser C (Appl Stat) 28(1):100-108

The invention claimed is:

1. A method of using a computer system to assist in planning a trajectory for a surgical insertion into a skull to a target representing an anatomical region, the method comprising:
providing the computer system with a three-dimensional image representation of the skull and brain which has been parcellated into anatomical regions, including an identification of critical objects comprising structures within the brain to be avoided during the surgical insertion;
providing the computer system with a region of interest corresponding to a target anatomical region within the brain representing the target of the trajectory for the surgical insertion, said target anatomical region corresponding to an anatomical structure of the brain;
determining a metric for voxel locations within the target anatomical region, the metric being based on the target anatomical region and representing the suitability of each of the voxel locations to be a target location for the trajectory, the metric being further based on distance inside the region of interest, such that the suitability of a voxel location increases with distance inside the region of interest;
based on the metric, selecting a set of one or more voxel locations having the greatest suitability according to the metric within the region of interest, each of the one or more selected voxel locations representing a potential target location for the trajectory, wherein the set of one or more voxel locations comprises multiple voxel locations, each voxel location in the set corresponding to a respective potential target location, and each voxel location in the set representing a local maximum of the metric; and
identifying a trajectory for the surgical insertion to a potential target location in the region of interest.

2. The method of claim 1, wherein the set of one or more voxel locations comprises multiple voxel locations, each corresponding to a respective potential target location, and wherein identifying a trajectory comprises:
for each of the potential target locations, determining one or more trajectories to that potential target location; and
selecting the trajectory for the surgical insertion from the determined trajectories to the multiple potential target locations.

3. The method of claim 2, further comprising:
for each of the potential target locations, determining multiple trajectories to that potential target location;
for each of the potential target locations, identifying an optimal trajectory to that potential target location from said multiple trajectories; and
selecting the trajectory for the surgical insertion from the optimal trajectories to the multiple potential target locations.

4. The method of claim 1, wherein the selection of the trajectory for the surgical insertion from the determined or optimal trajectories is based on at least trying to minimise a risk factor associated with the trajectories.

5. The method of claim 1, wherein the metric is independent of any trajectory leading to the voxel location for which the metric is being calculated.

6. The method of claim 1, wherein the metric is based on at least one of:
distance from the nearest critical objects, such that the suitability of a voxel location increases with distance from the nearest surface of the critical objects;
proximity to a medial surface of the region of interest, such that the suitability of a voxel location within the region of interest increases with closeness to the medial surface; and
a weighted sum of a first factor representing distance inside the region of interest and a second factor based on distance from the nearest surface of the critical objects.

7. The method of claim 1, further comprising imposing a constraint on selecting the set of one or more voxel locations to represent potential target locations, said constraint requiring a predetermined minimum distance between the potential target locations within the region of interest.

8. The method of claim 1, wherein said selecting a set of one or more voxel locations includes:
generating a set of multiple candidate voxel locations; and
spatially clustering the multiple candidate voxel locations.

9. The method of claim 8, wherein N electrodes (N>1) are to be inserted into said region of interest, and said spatial clustering is configured to form N clusters, each cluster corresponding to a respective electrode for insertion.

10. The method of claim 8, wherein selecting a set of one or more voxel locations comprises selecting one or more voxel locations for each cluster from said spatial clustering.

11. The method of claim 10, wherein, for each cluster, the one or more voxel locations are selected that have the largest suitability according to the metric.

12. The method of claim 8, wherein the set of multiple candidate voxel locations is generated by iterative flooding.

13. The method of claim 1, further comprising providing multiple regions of interest, and selecting a respective trajectory for each region of interest.

14. The method of claim 13, wherein the trajectories for the regions of interest are subject to a constraint to reduce potential interference between trajectories to regions of interest.

15. The method of claim 1, wherein the set of one or more voxel locations comprises M voxel locations, each corresponding to a respective potential target location, where M is in the range 3 to 50, preferably 5 to 25, preferably 8 to 15.

16. The method of claim 1, wherein the three-dimensional image representation comprises data from computed tomography and/or magnetic resonance imaging.

17. The method of claim 1, wherein the surgical insertion is to be used for implanting an electrode into the skull.

18. A non-transitory computer-readable medium comprising program instructions in machine-readable format that when executed by one or more processors in a computer system cause the computer system to implement the method of claim 1.

19. A computer system to assist in planning a trajectory for a surgical insertion into a skull to a target representing an anatomical region, the computer system being configured to:

provide the computer system with a three-dimensional image representation of the skull which has been parcellated into anatomical regions, including an identification of critical objects comprising structures within the skull to be avoided during the surgical insertion;

provide the computer system with a region of interest corresponding to a target anatomical region within the skull representing the target of the trajectory for the surgical insertion, said target anatomical region corresponding to an anatomical structure of the brain;

determine a metric for voxel locations within the target anatomical region, the metric being based on the target anatomical region and representing the suitability of each of the voxel locations to be a target location for the trajectory, the metric being further based on distance inside the region of interest, such that the suitability of a voxel location increases with distance inside the region of interest;

based on the metric, select a set of one or more voxel locations having the greatest suitability according to the metric within the region of interest, each of the one or more selected voxel locations representing a potential target location for the trajectory, wherein the set of one or more voxel locations comprises multiple voxel locations, each voxel location in the set corresponding to a respective potential target location, and each voxel location in the set representing a local maximum of the metric; and identify a trajectory for the surgical insertion to a potential target location in the region of interest.

* * * * *